United States Patent [19]

Wood

[11] 4,038,334
[45] July 26, 1977

[54] FRACTIONAL DISTILLATION PRESSURE CONTROL FOR SEPARATION OF AROMATIC ALKYLATION PRODUCT

[75] Inventor: Charles E. Wood, Palatine, Ill.

[73] Assignee: UOP Inc., Des Plaines, Ill.

[21] Appl. No.: 699,747

[22] Filed: June 24, 1976

[51] Int. Cl.² .................... C07C 3/56; C07C 15/09
[52] U.S. Cl. .................... 260/671 R; 202/160; 203/2; 260/671 P
[58] Field of Search .............. 260/671 R, 671 P; 202/160; 203/2; 208/DIG. 1

[56] References Cited

U.S. PATENT DOCUMENTS

| | | | |
|---|---|---|---|
| 2,995,611 | 8/1961 | Linn et al. | 260/671 R |
| 3,423,291 | 1/1969 | Oglesby | 203/2 |
| 3,427,228 | 2/1969 | Constantikes et al. | 203/2 |
| 3,444,052 | 5/1969 | Bracken et al. | 203/2 |
| 3,520,944 | 7/1970 | Ward | 260/671 R |

Primary Examiner—Herbert Levine
Attorney, Agent, or Firm—James R. Hoatson, Jr.; William H. Page, II; Robert W. Erickson

[57] ABSTRACT

A pressure control system and method for utilization in a process for effecting the alkylation of an aromatic hydrocarbon with a normally gaseous olefinic feed stream. The system is intended to control the pressure within a fractional distillation column which initially recovers the alkylaromatic product from unreacted aromatic hydrocarbons and a minor quantity of normally gaseous paraffinic contaminants contained in the olefinic feed stream. The system is especially advantageous in the boron trifluoride-catalyzed alkylation of benzene with ethylene, the latter containing minor quantities of ethane which must necessarily be vented, or removed from the system.

11 Claims, 1 Drawing Figure

FRACTIONAL DISTILLATION PRESSURE CONTROL FOR SEPARATION OF AROMATIC ALKYLATION PRODUCT

APPLICABILITY OF INVENTION

Processes for effecting the alkylation of an aromatic hydrocarbon with a normally gaseous olefinic hydrocarbon, find widespread utilization throughout the petroleum and petrochemical industries. For example, the alkylation of toluene with an ethylene feed stream results in methyl-ethyl benzene (ethyltoluene) which is principally utilized as an intermediate in the preparation of vinyl toluene, indene, para-ethyl toluene sulfonate, etc. Benzene is often alkylated with propylene for the production of isopropyl benzene (cumene), which, upon oxidation, produces cumene hydroperoxide; di-isopropyl benzene is oxidized to terephthalic acid, a starting material for many synthetic fiber products. Benzene is often alkylated with an ethylene-rich feed to produce ethylbenzene, a desired chemical intermediate whose principal use is in the production of styrene, via dehydrogenation. Other processes involve the production of alkylaromatics for use as starting materials in the manufacture of resins, plastics, detergents, elastomers, etc.

Aromatic hydrocarbons, benzene, toluene, the xylenes and/or ethylbenzene, are alkylated with a normally gaseous olefinic feed stream of ethylene, propylene, butylene and/or isobutylene. As hereinafter indicated, the alkylation reactions have been effected in the presence of a plurality of catalysts including solid phosphoric acid, a mixture of hydrogen fluoride and boron trifluoride, Friedel-Crafts metal halides, such as aluminum trichloride. Since the advent of the aromatic alkylation process, catalyst development appears to have culminated in a preference for a catalytic composite comprising boron halide-modified refractory inorganic oxide, and particularly a boron trifluoride-modified alumina. The alkylation reaction zone effluent is subject to a series of separations to recover the desired alkylated aromatic hydrocarbons while segregating the unreacted aromatic hydrocarbon and any poly-alkylated hydrocarbons formed during the process. Generally, the reaction zone effluent is initially separated to recover the alkylated aromatics from the unreacted aromatic feed components. Most commonly, this is accomplished through the use of a fractional distillation column, the functioning pressure of which must be very carefully controlled in order to attain the desired product purity and recovery. As hereinafter indicated in greater detail, the inclusion of relatively minor quantities of normally gaseous paraffins, within the olefinic feed stream, renders control of the fractional distillation column pressure extremely difficult.

The invention herein described is intended for utilization in an aromatic alkylation process, and is intended to afford control of the pressure within the fractional distillation column which initially recovers the alkylaromatic product from unreacted aromatic hydrocarbons and the minor quantity of normally gaseous paraffinic contaminants. My system is especially advantageous in the boron trifluoride-catalyzed alkylation of benzene with ethylene, the latter containing minor quantities of ethane which must necessarily be vented, or removed from the process.

OBJECTS AND EMBODIMENTS

A principal object is to provide a distillation column pressure control system for utilization in an aromatic alkylation process. A corollary objective of my invention is to eliminate significant pressure cycles in a fractional distillation column while separating non-alkylated aromatic hydrocarbons from alkylated aromatic hydrocarbons.

Another object resides in the control of a distillation column pressure while separating ethylbenzenes from unreacted benzene and an ethane contaminant.

A specific object is to improve reaction product separation in an aromatic alkylation process effected in contact with a catalytic composite comprising a boron halide.

Therefore, in one embodiment, the invention herein described is directed toward a process for alkylating an aromatic hydrocarbon with a normally gaseous olefinic feed stream containing a normally gaseous paraffinic contaminant, in an alkylation reaction zone and in contact with an alkylation catalyst comprising a boron halide-modified refractory inorganic oxide, to produce an alkylated aromatic hydrocarbon, in which process (1) alkylation reaction product effluent is separated, in a fractional distillation column, to provide a first liquid-phase of an alkylated aromatic concentrate, containing poly-alkylated aromatics, and first vapor-phase of an unreacted aromatic concentrate, containing boron halide and said paraffinic contaminant; (2) said first vaporous phase is separated, in a separation zone, to provide a second liquid-phase, unreacted aromatic concentrate and a second vapor-phase rich in paraffinic contaminant and boron halide; and, (3) a first portion of said second vapor-phase is returned to said distillation column, a second portion is recycled to said alkylation reaction zone, a third portion is treated, in a treating zone, to remove boron halide and at least a portion of the resulting paraffinic contaminant-rich vapors are withdrawn from the process; the method of controlling the fractional distillation column pressure which comprises the steps of: (a) sensing the pressure in said distillation column at a locus proximate to the withdrawal of said unreacted aromatic vapor-phase concentrate; (b) developing a first signal representative of said distillation column pressure; (c) adjusting the flow rate of the second portion of said second vapor phase being recycled to said alkylation reaction zone responsive to said first signal; (d) developing a second signal representing the flow rate of the recycled portion of said second vapor phase; and, (e) regulating the quantity of said paraffinic contaminant-rich vapors withdrawn from said process responsive to said second signal.

In another embodiment, my invention is directed toward a process for alkylating an aromatic hydrocarbon with a normally gaseous olefinic feed stream containing a normally gaseous paraffinic contaminant, in an alkylation reaction zone and in contact with an alkylation catalyst comprising boron trifluoride-modified alumina, to produce a mono-alkylated aromatic hydrocarbon, in which process (1) alkylation reaction product effluent is separated, in a first fractional distillation column, to provide a first liquid-phase of an alkylated aromatic concentrate, containing poly-alkylated aromatic hydrocarbons, and a first vapor-phase of an unreacted aromatic concentrate, containing boron trifluoride and said paraffinic contaminants; (2) said first liquid-phase is separated, in a second fractional distillation column, to recover said alkylated aromatic concentrate and to provide a poly-alkylated aromatic concentrate; (3) said poly-alkylated aromatic concentrate is reacted, in a transalkylation reaction zone and in contact with a transalkylation catalyst comprising boron trifluoride-modified alumina to produce additional mono-alkylated aromatic hydrocarbons; (4) said first vaporous phase is separated, in a separation zone, to provide a second liquid-phase, unreacted aromatic concentrate and a second vapor-phase rich in paraffinic contaminants and boron trifluoride; (5) a first portion of said second vapor-phase is returned to said first fractional distillation column, a second portion is recycled to said alkylation reaction zone, a third portion is recycled to said transalkylation reaction zone, a fourth portion is treated, in a treating zone, to remove boron trifluoride, and at least a portion of the resulting paraffinic contaminant-rich vapors are withdrawn from the process; the method of controlling the first fractional distillation column pressure which comprises the steps of: (a) sensing the pressure in said distillation column at a locus proximate to the withdrawal therefrom of said first vapor-phase of unreacted aromatic concentrate; (b) developing a first signal representative of said distillation column pressure; (c) maintaining the flow rate of the third portion of said second vapor-phase, being recycled to said transalkylation reaction zone, substantially constant; (d) adjusting the flow rate of the second portion of said second vapor-phase, being recycled to said alkylation reaction zone, responsive to said first signal; (e) sensing the flow rate of the second portion of said second vapor-phase and developing a second signal representative thereof; and, (f) adjusting the quantity of said paraffinic concentrate-rich vapors, withdrawn from said process, responsive to said second signal.

In a specific embodiment, the present invention involves a process for alkylating benzene with an ethylene feed stream containing ethane, in an alkylation reaction zone and in contact with an alkylation catalyst comprising boron trifluoride-modified alumina, to produce ethylbenzene, in which process (1) alkylation reaction product effluent is separated, in a first fractional distillation column, to provide a first liquid-phase of an ethylbenzene concentrate, containing polyethylbenzenes, and a first vapor-phase of an unreacted benzene concentrate, containing boron trifluoride and ethane; (2) said first liquid-phase is separated, in a second fractional distillation column, to recover said ethylbenzene and to provide a polyethylbenzene concentrate; (3) said polyethylbenzene concentrate is reacted, in a transalkylation reaction zone and in contact with a transalkylation catalyst comprising boron trifluoride-modified alumina, to produce additional ethylbenzene; (4) said first vaporous phase is separated, in a separation zone, to provide a second liquid-phase of benzene and a second vapor-phase rich in ethane and boron trifluoride; (5) a first portion of said second vapor-phase is returned to said first fractional distillation column, a second portion is recycled to said alkylation reaction zone, a third portion is recycled to said transalkylation reaction zone, a fourth portion is treated, in a treating zone, to remove boron trifluoride, and at least a portion of the resulting ethane-rich vapors are withdrawn from the process, the method of controlling the first fractional distillation column pressure which comprises the steps of: (a) sensing the pressure in said first distillation column at a locus proximate to the withdrawal therefrom of said first vapor-phase of the benzene concentrate; (b) developing a first signal representative of said first distillation column pressure; (c) maintaining the flow rate of the third portion of said second vapor-phase, being recycled to said transalkylation reaction zone, substantially constant; (d) adjusting the flow rate of the second portion of said second vapor-phase, being recycled to said alkylation reaction zone, responsive to said first signal; (e) sensing the flow rate of the second portion of said second vapor-phase and developing a second signal representative thereof; and, (f) adjusting the quantity of said ethane-rich vapors, withdrawn from said process, responsive to said second signal.

These, as well as other objects and embodiments will become evident from the following more detailed description of the pressure control method encompassed by the present invention. In one such other embodiment, the product effluent from both the alkylation reaction zone and the transalkylation reaction zone are introduced into the fractional distillation column.

PRIOR ART

It must be recognized that the prior art proliferates in a wide spectrum of processes for alkylating an aromatic hydrocarbon with an olefinic feed stream. Such processes involve a variety of processing techniques, catalysts and combinations of aromatic and olefinic hydrocarbons. No attempt will be made herein to delineate exhaustively the appropriate published literature; it will suffice simply to note several examples which appear to be exemplary of prior art practices and procedures, and to which the present invention is intended to be applied. The greater majority of aromatic alkylation processes indicate a distinct preference for a catalyst comprising a Friedel-Crafts metal halide, generally composited with a refractory inorganic metal oxide, and especially a catalyst of boron trifluoride-modified alumina.

In U.S. Pat. No. 2,778,862 (Cl. 260-671), issued Jan. 22, 1957, toluene is alkylated with ethylene in the presence of aluminum chloride to produce primarily mono-ethyltoluene isomers, with the meta isomer predominating. The process is effected at particular operating conditions which minimize the production of benzene, ethylbenzene and poly-methyl derivatives of toluene.

Rearrangement of certain secondary alkylbenzenes, particularly the disproportionation of isopropylbenzene and secondary butylbenzenes, is the subject of U.S. Pat. No. 2,852,575 (Cl. 260-671), issued Sept. 16, 1958. The catalyst constitutes boron trifluoride and liquid hydrogen fluoride utilized under substantially anhydrous conditions. A plurality of fractional distillation columns is employed in separating the reaction product effluent into its various components including the desired di-isopropyl benzene product.

U.S. Pat. No. 2,860,173 (Cl. 260-671), issued Nov. 11, 1958, proposes the production of mono-isopropylbenzene (cumene) by the alkylation of benzene with propylene in the presence of solid phosphoric acid catalyst. The novelty appears to reside in the utilization of a plurality of successive catalyst beds in which the catalyst is so proportioned that the temperature rise in a given bed does not exceed a specified limit. Two distillation columns are utilized first to depropanize the reaction product effluent, and then to recover unreacted benzene from the mono-isopropylbenzene product.

In U.S. Pat. No. 2,971,992 (Cl. 260-671), issued Feb. 14, 1961, the alkylation of benzene is effected utilizing a mixture of ethylene and propylene, in combination with unreacted gases including paraffins, principally to produce ethylbenzene and cumene. One absorber and four fractional distillation columns are utilized in separating the reaction product effluent to recover the desired products. The absorber removes boron trifluoride from the normally gaseous contaminants which are vented; additional paraffinic contaminants are vented from the first distillation column employed to recover the unreacted benzene. The second and third columns are designed to recover the ethylbenzene and cumene products, while the fourth column is utilized to remove tar and higher-boiling polyalkylaromatic hydrocarbons from the process. With respect to the alkylation reaction zone, it is recognized that the same may be packed with a refractory inorganic oxide, and preferably alumina.

A process for the alkylation of benzene with ethylene and/or propylene is described in U.S. Pat. No. 2,995,611 (Cl. 260–671), issued Aug. 8, 1961. Following the utilization of three fractionating columns in the separation of the reaction product effluent, a second reaction zone is utilized to foster transalkylation reactions for the purpose of producing additional ethylbenzene. The catalytic composite, in both reaction zones, constitutes a refractory inorganic oxide, preferably alumina, modified with boron trifluoride.

The aromatic alkylation process described in U.S. Pat. No. 3,631,122 (Cl. 260-671), issued Dec. 28, 1971, is primarily concerned with a technique for removing non-volatile boron oxide hydrates produced during the alkylation reaction. With respect to the flow of material throughout the process, the effluent from the alkylation reaction zone is combined with the effluent from the transalkylation zone and introduced therewith into the benzene column, the bottoms from which are introduced into the ethylbenzene column for the recovery of the ethylbenzene product and to supply the polyethylbenzenes for use as charged to the transalkylation reaction zone.

U.S. Pat. No. 3,894,090 (Cl. 260-671), issued July 8, 1975, offers another illustration of the combination of alkylation and transalkylation, with emphasis being placed upon the elimination of boron oxide hydrates.

SUMMARY OF INVENTION

In the interest of brevity, and without the intent to unduly limit my invention beyond the scope and spirit of the appended claims, further description of the present pressure control method will be directed toward the alkylation of benzene with ethylene to produce ethylbenzene. Also, although intended for integration into processes employing a variety of catalysts, the following discussion will involve a process which utilizes boron trifluoride-modified alumina, which catalyst appears to enjoy current prominence in the art. Perusal of the foregoing exemplary art relative to aromatic/olefin alkylation, reveals nothing with respect to the present invention — the control of the initial fractional distillation column pressure. While recognizing the existence of ethane contaminant in the ethylene feed, for example in a process for benzene alkylation, and the removal thereof from the process, the art appears to be totally unaware of the difficulties attendant pressure control of the benzene column which is vital to obtaining acceptable separation of the alkylation zone effluent. In regard to the ethylene feed stream, present-day techniques used in obtaining the same have resulted in substantially greater ethylene purity. That is, it is now uncommon to have a feed stream whose ethylene content is less than about 98.0 mole percent; conversely, an ethane (plus other inerts) concentration greater than 2.0 mole percent.

As a general practice, pressure control of a distillation column has been, and continues to be accomplished by adjusting the flow of vapors vented from the process (directly from the overhead receiver system attendant the distillation column) in response to changes in the pressure monitored proximate to the locus of overhead withdrawal. Such a basic control system is inadequate and impractical for use in current benzene alkylation processes in view of the fact that the vented vaporous stream will contain unreacted benzene and boron trifluoride which economical considerations dictate must be recovered and recycled within the process. Therefore, the only vaporous material vented from the process system constitutes the ethane contaminant. As will immediately be recognized by those having the requisite expertise, judicious operating techniques require venting an amount which is not greater than that which is introduced with the ethylene feed stream. As previously stated, the amount of ethane rarely exceeds 2.0 mole percent, and often is considerably less. Attempts to control benzene column pressure by adjustments in a flow rate which is necessarily extremely small, do not succeed in eliminating significantly detrimental pressure cycling. To illustrate, as hereinafter set forth in a specific example, an ethylene-rich feed stream, in the amount of about 936.08 lb-moles/hr. (425.49 kg-moles/hr.) contains about 0.96 lb-moles/hr. (0.44 kg-moles/hr.) of ethane and other inerts, or an ethylene purity of about 99.9%. The overhead vapors from the initial fractional distillation column (in an ethylbenzene process, the benzene column) are in an amount of about 6282.95 lb-moles/hr. (2855.89 kg-moles/hr.). Of this quantity, only 176.18 lb-moles/hr. (80.08 kg-moles/hr.) are introduced into the circulating compressor which recycles the greater proportion thereof to the alkylation and transalkylation reaction zones. Since the amount of vapors vented from the overall system must necessarily approximate the quantity of the vaporous paraffinic contaminants, and other inerts, only 0.54% of the material introduced into the compressor is withdrawn from the process. It will be readily ascertained that acceptable control of the benzene column pressure cannot be obtained by adjustments in this stream. Obviously, the desired stream purities and product recovery are virtually impossible to achieve.

This situation is further compounded by the fact that the initial separation of ethylbenzene and polyethylbenzenes from unreacted benzene is effected in a column having a relatively large number of trays, or decks, and which functions at relatively low pressures. In one instance, a column having a total of 70 trays is maintained at a bottom pressure of about 45 psig. (4.06 atm.) and a top pressure of about 35 psig. (3.38 atm.), or a pressure differential, over the 70 trays of 10 psi. (0.68 atm.). Pressure surges, from significant changes in the vapor loading throughout the column, in turn stemming from a variety of changes in other variables, simply cannot be controlled by adjusting the rate of vented vapor flow while maintaining stream purities. In essence, the pressure control method herein described allows vapor surges to proceed through the system without incurring detrimentally large cycling of the benzene column pressure.

Although the present invention is primarily concerned with the initial separation of the alkylation reaction system product, including both an alkylation and transalkylation reaction zone, a relatively brief description of an entire process is deemed warranted for the sake of completeness and to illustrate further the applicability of the pressure control method herein described. Furthermore, although not with the intent to restrict the present invention beyond the scope and spirit of the appended claims, the description which follows will be specifically directed toward an aromatic alkylation process intended to maximize the production of ethylbenzene from a feed stream comprising ethylene and benzene. It will be presumed that the reactions carried out in both the alkylation and transalkylation zones are effected utilizing a boron trifluoride-modified alumina; as previously stated, this catalyst is preferred in aromatic alkylation processes.

As a practical matter, the catalyst in both the alkylation and transalkylation reaction zones is boron trifluoride-modified alumina. Boron trifluoride is a gaseous material boiling at about −101° C., and is at least somewhat soluble in most of the common organic solvents. Generally, boron trifluoride is utilized as a pure vaporous material by direct passage of the gas to the reaction zones so that it dissolves, at least partially, in the aromatic feed stream. Although an organic solvent solution of $BF_3$ may be employed, such technique is not preferred since $BF_3$ complexes with a multitude of organic compounds and the latter can react with either the aromatic, or olefinic feed stream. Required quantities of $BF_3$ are relatively small, and may be conveniently expressed as grams of $BF_3$ per mole of olefin. Thus, the quantity of $BF_3$ may be less than 1.0 gram per gram-mole of olefin, and preferably from 0.1 to 1.0 gram per gram-mole. When this amount is present in the reaction zones, essentially all of the ethylene will be reacted, even when present in minor, or dilute amounts in a refinery off-gas stream.

The benzene, or other aromatic hydrocarbon, will be present in a molar excess with respect to the ethylene, or other olefinic compound. On a mole basis, the ratio is generally in the range of 1.5:1.0 to about 20.0:1.0, and preferably from 2.0:1.0 to about 15.0:1.0. From the technical viewpoint, the excess benzene tends to reduce the quantity of polyethylbenzenes (PEB) formed, especially those containing more than two ethyl groups. Also, the possibility of olefin (ethylene) polymerization is significantly reduced. Alkylation of benzene with ethylene is effected at reaction zone temperatures ranging from 100° F. (37.8° C.) to about 600° F. (315° C.), and preferably from about 250° F. (121° C.) to about 450° F. (232° C.). Transalkylation reactions, designed to produce additional ethylbenzene from PEB, are generally effected at slightly elevated temperatures in the range of 200° F. (93° C.) to about 700° F. (371° C.), and preferably from 350° F. (177° C.) to about 500° F. (260° C.). Transalkylation of PEB's, including di-, tri-, tetra-, penta- and hexa-ethylbenzene, is really neither exothermic, nor endothermic, and proceeds at a much slower rate than the initial alkylation reactions. Therefore, in order to obtain virtually complete conversion of the PEB's, the charge to the transalkylation reaction zone is generally more than three times the net PEB make. Pressures in the reaction zones will range from about 0 psig. (1.0 atm.) to about 1,500 psig. (103.1 atm.), and preferably from 300 psig. (21.4 atm.) to 600 psig. (41.8 atm.). Generally, the pressure is selected to maintain the benzene charge in liquid phase in the reaction zone. The liquid hourly space velocity may vary between about 0.5 to about 10.0. Within the transalkylation reaction zone, an excess of benzene over the polyethylbenzenes is maintained, with the relative ratio being from about 0.5:1.0 to about 3.0:1.0, on a mole basis.

The effluent streams from both the alkylation and transalkylation reaction zones are introduced into a fractional distillation zone, hereinafter referred to as the "benzene column", for the purpose of separating ethylbenzene (including PEB's) from the unreacted benzene. The latter is removed as a vapor, and contains boron trifluoride catalyst, ethane and other inerts. The benzene column will function at a bottoms pressure of about 25 psig. (2.70 atm.) to about 65 psig. (5.42 atm.) and a top pressure in the range of about 15 psig. (2.02 atm.) to about 55 psig. (4.74 atm.). Reboiler section temperatures will range from about 300° F. (149° C.) to 500° F. (260° C.), while the top temperature is normally in the range of 150° F. (65° C.) to about 350° F. (177° C.). As hereinbefore set forth, the present inventive concept encompasses a technique for controlling benzene column pressure which avoids the deleterious effects (directed to separation efficiency and stream purities) otherwise stemming from significant pressure cycling.

Normally liquid ethylbenzene product, containing PEB's, as recovered from the reboiler section of the benzene column is introduced into a second fractional distillation column herein referred to as the "ethylbenzene column". The purpose of the ethylbenzene column is to recover ethylbenzene from the polyethylbenzenes, and it normally functions at a bottom pressure of about 15 psig. (2.02 atm.) to about 35 psig. (3.38 atm.) and a top pressure in the range of about 5 psig. (1.34 atm.) to about 25 psig. (2.70 atm.). The reboiler section temperature will be about 350° F. (177° C.) to about 550° F. (288° C.), while the top temperature will range from about 225° F. (107° C.) to about 425° F. (218° C.). Polyethylbenzenes are recovered as a bottoms product, and constitute the feed stream to the transalkylation reaction zone. As a standard practice, the feed stream is first introduced into a "PEB stripper column" in order to remove therefrom heavier polymers and tar products. The latter stem primarily from the presence in the ethylene feed of propylene and/or acetylene which will react with benzene to form polyisopropylbenzene and diphenyl ethane. These compounds further react to produce the heavier tars and polymers which are removed from the process from the PEB column, or stripper. Stripping vapors, needed to strip the polyethylbenzenes from the tars and polymers, is supplied by externally reboiling a portion of the reboiler section bottoms liquid. The PEB column integrated into most aromatic alkylation functions at relatively low pressures from 0 psig. (1.0 atm.) to about 20 psig. (2.36 atm.). Temperatures are comparatively higher, and range from about 450° F. (232° C.) to about 650° F. (343° C.) in the reboiler section, and from about 300° F. (149° C.) to about 500° F. (260° C.) at the top of the column.

The vaporous overhead material from the benzene column is cooled and condensed to a temperature of about 60° F. (15.6° C.) to about 140° F. (60° C.), and is introduced into the benzene column overhead receiver system. Condensed liquid is withdrawn, principally benzene, and the greater proportion returned to the upper section of the column as the external reflux stream. The uses of the remaining portion of the condensed material are hereinafter described in conjunction with the description of the accompanying drawing. The vaporous phase from the benzene column overhead receiver has a typical composition of about 54.0% benzene, 32.2% inert material and 13.8% boron trifluoride, on a mole basis. Subsequent treatment of the overhead stream involves the recovery of the benzene and boron trifluoride, accompanied by removal, or venting from the process of so much of the vaporous inert material that had been introduced with the ethylene feed stream. As commonly practiced, use is made of a reciprocating compressor having a plurality of stages with intermediate suction and discharge drums, or knock-out pots. Generally, the liquid phases recovered from these drums and/or knock-out pots is reintroduced into the benzene column overhead receiver. However, another common practice involves removing at least a portion of the liquid phases from the process through an alumina treater in order to prevent the build-up of borates and complexes thereof with $BF_3$. Where this precaution is not followed, these materials precipitate as solids in the benzene column and ultimately result in the malfunction thereof.

Figure 1:
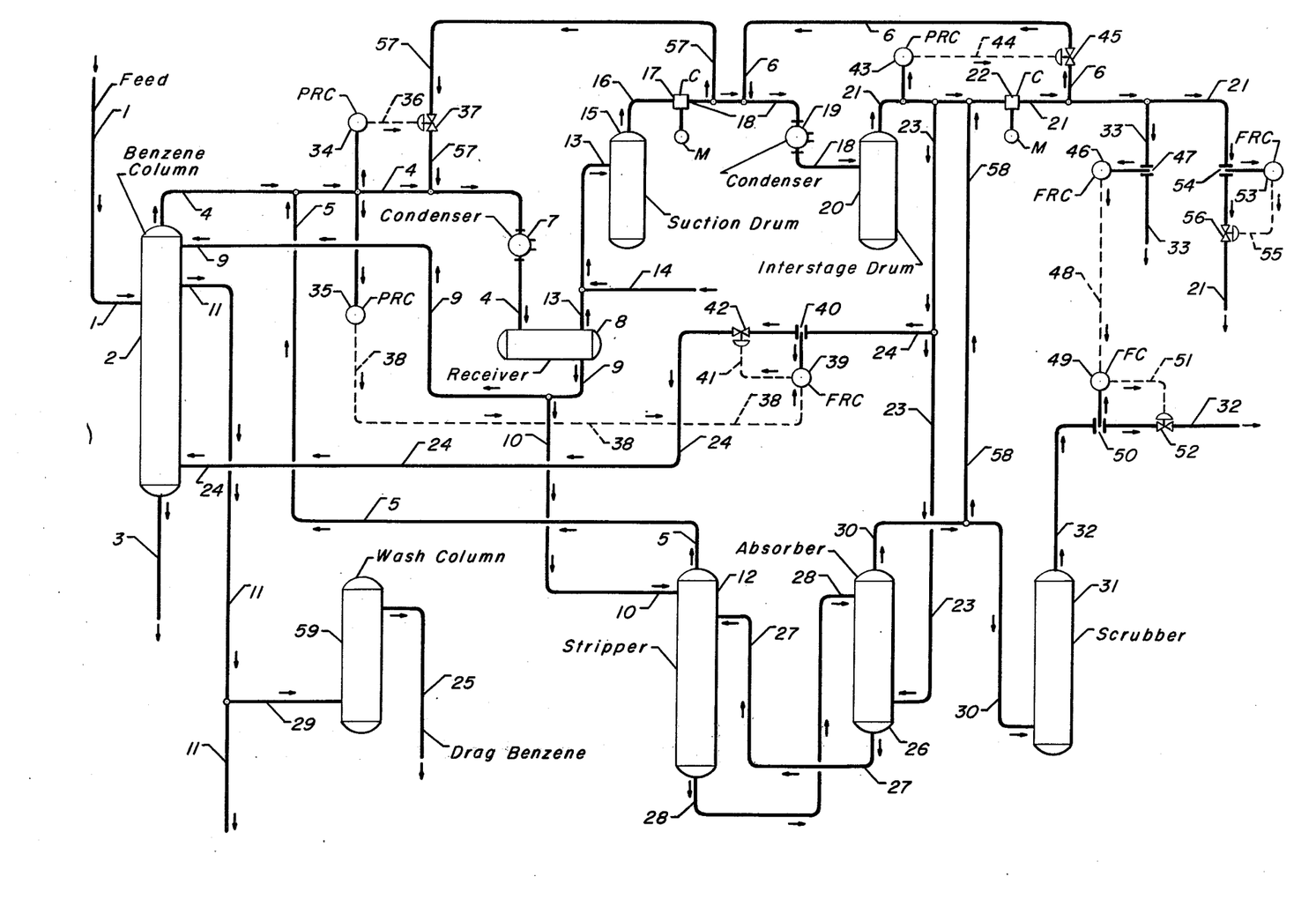

Considering a two-stage reciprocating compressor, as is illustrated in the accompanying drawing, a portion of the vaporous material from the first stage may be "spilled-back" to the overhead system for introduction into the overhead receiver. The remainder is condensed and introduced into an interstage drum from which a portion is diverted into a boron trifluoride absorber column for recovery of $BF_3$ prior to venting the inert-rich material. Excess $BF_3$ vapors are introduced into the second stage of the compressor from the absorber. Vaporous $BF_3$, including inerts and some benzene, is returned to a lower section of the benzene column as a stripping medium to remove borates and $BF_3$ complexes. With respect to the vaporous material from the second compression stage, the greater proportion is returned to the alkylation and transalkylation reaction zones, and any excess is spilled back to the discharge of the first stage compression.

By way of summarizing the foregoing, the normally liquid portion of the benzene column overhead is used as reflux to the column, as stripping medium in the $BF_3$ stripping column and as a so-called "drag benzene" stream for the removal of borates and $BF_3$ complexes. Vaporous material is recycled in part to both the alkylation and transalkylation zones, a portion is returned to the benzene column overhead receiver and a portion is vented from the system to purge the latter of inert material and thus prevent a build-up thereof.

As previously stated, my invention is directed toward a technique for controlling benzene column pressure in a manner which reduces, or eliminates wide pressure cycling, notwithstanding the extremely minor quantity of overhead vaporous material removed from the system. In the illustrative example which follows, the total amount of vaporous material introduced into the initial stage of a reciprocating compressor is about 7,478 lbs./hr. (3,399 kg/hr.); of this, only about 28 lbs./hr. (12.7 kg./hr.) are vented to prevent the build-up of inerts within the system. Any attempt to control benzene column pressure by adjusting the rate of this vent stream in direct response to a generated signal which is representative of the variance between the existing column pressure and the specified column pressure does not succeed.

In further describing my invention, reference will be made to the accompanying drawing which is presented for the sole purpose of illustrating a typical benzene column separation system found in present-day processes for producing ethylbenzene, having the control method integrated therein. In the drawing, the method is presented by way of a simplified, schematic flow diagram in which many details such as pumps, instrumentation and other controls, heat-exchange and heat-recovery circuits, valving, start-up lines and similar hardware have been eliminated, or reduced in number as non-essential to an understanding of the techniques involved. The use of such miscellaneous appurtenances, to modify the process as illustrated, will be evident to those possessing the requisite skill in the art of petroleum refining technology.

DESCRIPTION OF DRAWING

Briefly, with reference to the drawing, the venting of the inert-rich material through line 32 is controlled through control valve 52, the degree of change in the opening of which is adjusted in response to a signal generated by Flow Controller (FC) 49 and transmitted by way of instrument line 51. Flow Recorder Controller (FRC) 46 senses the rate of vaporous flow in line 33 by way of orifice meter 47. This rate, as hereinafter set forth, varies in accordance with benzene column 2 pressure changes. A signal is developed by FRC 46 which represents the rate of vapor flow through line 33, and this signal is transmitted by way of instrument line 48 to reset the adjustable set point of FC 46. The latter compares the changed set point with the flow rate sensed by orifice plate 50, and makes the appropriate minor adjustment in control valve 52 through instrument line 51. The foregoing, regardless of which other process stream is adjusted responsive to the signal representing benzene column pressure, constitutes the inventive concept upon which the present novel control method is founded.

More specifically, the accompanying drawing will be described in conjunction with a commercially-scaled unit designed to maximize the production of ethylbenzene from 73,905 lbs/hr. (33,593 kg/hr.) of fresh benzene feed, having a purity of 99.84 mole percent, and 26,256 lbs/hr. (11,934 kg/hr.) of ethylene. On a mole basis, the latter contains about 0.10 percent of inert material (principally ethane) and about 0.001 percent of acetylene and propylene. The reaction section of the overall processing system forms no essential part of the pressure control method encompassed by the present invention. However, in order to be complete and to provide background for the benzene column pressure control technique, a brief description is believed warranted. The reaction section makes use of both an alkylation reaction zone and a transalkylation reaction zone, each of which utilizes both benzene recycle and boron trifluoride recycle. With respect to the alkylation reaction zone, the benzene-rich recycle is 148,923 lbs/hr. (67,692 kg/hr.) and the $BF_3$ recycle stream is in the amount of about 864 lbs/hr. (392.7 kg/hr.). Benzene is recycled to the transalkylation reaction zone in an amount of about 146,013 lbs/hr. (66,370 kg/hr.), while the $BF_3$ recycle is 2,371 lbs/hr. (1,078 kg/hr.). The feed stream to the latter also includes 59,048 lbs/hr. (26,840 kg/hr.) of polyethylbenzenes from the bottoms stream of the ethylbenzene column after the removal of about 684 lbs/hr. (311 kg/hr.) of tar and heavy polymers in the PEB stripper. The effluent streams from the alkylation and transalkylation reaction zones are combined to form the charge to the benzene column. A component analysis of the combined reaction zone effluent is presented in the following Table I: In this Table, di-ethylbenzene, tri-ethylbenzene, tetraethylbenzene, penta-ethylbenzene, hexa-ethylbenzene and di-propylbenzene have been, for convenience, collectively included as the polyethylbenzene stream. Also, the "saturates" collectively include the paraffins and naphthenes originating in the fresh charge stock and the benzene recycle streams to the two reaction zones; these are removed with the drag benzene stream in line 25.

TABLE I:

| Reaction Zone Combined Effluent | | |
|---|---|---|
| Component | Lb-moles/hr. | Kg-moles/hr. |
| Boron trifluoride | 20.43 | 9.29 |
| Ethane & Inerts | 62.94 | 28.61 |
| Saturates | 305.62 | 138.92 |
| Benzene | 3136.37 | 1425.62 |
| Ethylbenzene | 1165.84 | 529.93 |
| Cumene | 0.01 | — |
| Methyl-ethylbenzene | 0.16 | 0.07 |
| Polyethylbenzenes | 409.63 | 186.20 |

With particular reference now to the drawing, the effluent from the reaction zone section is introduced, via line 1, into benzene column 2, at a temperature of about 288° F. (142° C.) and a pressure of about 40 psig. (3.72 atm.). An ethylbenzene concentrate, in the amount of about 1,333.69 lb-moles/hr. (606.22 kg-moles/hr.), is withdrawn as a bottoms stream through line 3 at a temperature of about 413° F. (212° C.) and a pressure of about 45 psig. (4.06 atm.). The ethylbenzene stream has the component analysis shown in the following Table II: The ethylbenzene-rich stream is introduced into the ethylbenzene column (not illustrated), from which the desired ethylbenzene product is recovered as an overhead stream containing the small quantities of benzene, cumene and methylethylbenzene. The polyethylbenzenes are withdrawn as a bottoms product and introduced into the PEB stripper, from which 3.35 lb-moles/hr. (1.52 kg-moles/hr.) of tar and heavier polymer are removed from the system; the remaining 406.28 lb-moles/hr. (184.67 kg-moles/hr.) are recycled as feed to the transalkylation reaction zone.

TABLE II:

| Benzene Column Bottoms Stream | | |
|---|---|---|
| Component | Lb-moles/hr. | Kg-moles/hr. |
| Benzene | 0.36 | 0.16 |
| Ethylbenzene | 923.53 | 419.79 |
| Cumene | 0.01 | — |
| Methylethylbenzene | 0.16 | 0.07 |
| Polyethylbenzenes | 409.63 | 186.20 |

Also introduced into benzene column 2, via line 24, is a BF$_3$ recycle stream, in the amount of 77.05 lb-moles/hr. (35.02 kg-moles/hr.), the source of which is hereinafter set forth. On a mole basis, this BF$_3$ recycle stream comprises 4.3% benzene, 68.9% ethane plus inerts and 26.8% boron trifluoride. As previously stated, the purpose of this recycle stream, functioning as a stripping medium, is to inhibit the deposition of solids within the benzene column. A benzene-rich stream, in the amount of about 3,682.69 lb-moles/hr. (1,673.95 kg-moles/hr.) is withdrawn as a side-cut stream through line 11. The principal use of this stream is as benzene recycle to the two reaction zones; (1) 1,850.99 lb-moles/hr. (841.36 kg-moles/hr.) to the alkylation zone, and (2) 1,814.82 lb-moles/hr. (824.92 kg-moles/hr.) to the transalkylation reaction zone. However, prior to recycling these quantities, 16.88 lb-moles/hr. (7.67 kg-moles/hr.) are diverted through line 29 into wash column 59 in order to remove borates and/or BF$_3$ complexes from the system. The "drag" benzene stream is generally transported to suitable storage facilities by way of conduit 25.

Overhead vaporous material (including the benzene-rich reflux stream in line 9) is recovered through line 4, in the amount of about 6,282.95 lb-moles/hr. (2,855.89 kg-moles/hr.), at a temperature of about 256° F. (124° C.) and a pressure of about 35 psig. (3.38 atm.). This is combined with about 67.34 lb-moles/hr. (30.61 kg-moles/hr.) of a benzene-rich stream in line 5 which is obtained from BF$_3$ stripper 12 as hereafter indicated; on a mole basis, the stream in line 5 comprises 6.2% BF$_3$, 0.02% inerts (inclusive of ethane) and 93.6% benzene. The vaporous mixture continues through line 4 into condenser 7; the partially-condensed overhead stream, at a temperature of about 100° F. (38° C.) and a pressure of about 25 psig. (2.70 atm.), is introduced into receiver 8. Also introduced into receiver 8 are: 10.81 lb-moles/hr. (4.91 kg-moles/hr.) of liquid from compressor interstage drum 20, containing 92.0% benzene, 7.4% BF$_3$ and 0.6% inerts, on a mole basis; and, 185.23 lb-moles/hr. (84.20 kg-moles/hr.) of liquid from suction drum 15, containing 97.5% benzene, 0.2% inerts and 2.3% of boron trifluoride. Therefore, the total quantity of material being introduced into receiver 8 is 6,546.33 lb-moles/hr. (2,975.60 kg-moles/hr.), and comprises 96.2% benzene, 1.8% BF$_3$ and about 2.0% inerts.

The liquid phase from receiver 8 is withdrawn through line 9, and 63.89 lb-moles/hr. (29.04 kg-moles/hr.) are diverted into line 10 to be introduced thereby into BF$_3$ stripper 12. The remaining portion, 6.121.28 lb-moles/hr. (2,782.40 kg-moles/hr.) continue through line 9, and are introduced therethrough as reflux to benzene column 2. The vaporous material from receiver 8, in the amount of 361.16 lb-moles/hr. (164.16 kg-moles/hr.) are withdrawn through line 13, combined with 0.25 lb-moles/hr. (0.11 kg-moles/hr.) of make-up boron trifluoride from line 14 and introduced into compressor suction drum 15. As hereinbefore stated, 185.23 lb-moles/hr. (84.20 kg-moles/hr.) are removed (not illustrated) and reintroduced into overhead receiver 8. Vaporous material, in the amount of 176.18 lb-moles/hr. (80.08 kg-moles/hr.) is introduced via line 16 into the first stage 17 of the reciprocating compressor, at a temperature of about 100° F. (38° C.) and a pressure of about 25 psig. (2.70 atm.). The compressed vaporous material is combined with about 9.89 lb-moles/hr. (4.50 kg-moles/hr.) of spill-back vapors from line 6, the mixture continuing through line 18 into condenser 19 at a temperature of about 228° F. (108° C.) and a pressure approximating 90 psig. (7.12 atm.). The temperature is once again lowered to 100° F. (38° C.), and the vaporous material discharges into interstage drum 20. Liquid material, in the amount of 10.81 lb-moles/hr. (4.91 kg-moles/hr.) is withdrawn and reintroduced into receiver 8 (this conduit is not illustrated). Of the remaining 175.26 lb-moles/hr. (79.66 kg-moles/hr.), 91.06 lb-moles/hr. (41.39 kg-moles/hr.) are diverted through line 23. This amount constitutes the 77.05 lb-moles/hr. (35.02 kg-moles/hr.) of BF$_3$ recycled stripping vapors in line 24 (returned thereby to benzene column 2) and 14.01 lb-moles/hr. (6.37 kg-moles/hr.), inclusive of 233 lbs/hr. (105.91 kg/hr.) of BF$_3$, which continues through line 23 into BF$_3$ absorber 26, being introduced into the lower portion thereof.

An absorber lean oil, in the amount of 7,551 lbs/hr. (3,432.27 kg/hr.) is introduced via line 28 into the upper portion of absorber 26. The 233 lbs/hr. of BF₃ are absorbed therein, the rich absorber oil being recovered via line 27, and introduced thereby into BF₃ stripper 12. The BF₃ contained in the rich absorber oil is removed therefrom by the liquid material introduced from overhead receiver 8 via lines 9 and 10. Stripper vapors, in the amount of 67.34 lb-moles/hr. (30.61 kg-moles/hr.) are removed via line 5, and admixed thereby with the benzene column overhead vapors in line 4. The BF₃ lean oil, from the bottom portion of stripper 12, is withdrawn via line 28, and introduced thereby into BF₃ absorber 26. The total amount of absorber gas, 10.56 lb-moles/hr. (4.8 kg-moles/hr.) is recovered in line 30; of this amount, the excess which is not to be vented from the system, about 9.60 lb-moles/hr. (4.36 kg-moles/hr.), is diverted through line 58 to line 21, on the suction side of the second compression stage 22. The remainder, 0.96 lb-moles/hr. (0.44 kg-moles/hr.), continues through line 30 into caustic scrubber 31, and is ultimately removed from the process through line 32 which contains control valve 52. The total amount of vaporous material introduced into second compression stage 22 is 93.80 lb-moles/hr.; with the exception of the 9.89 lb-moles/hr. (4.50 kg-moles/hr.) which is spilled back by way of line 6, the vapors discharged from second stage 22 are recycled to the alkylation and transalkylation reaction zones. In this control method and in the illustration, the amount recycled through line 33 to the alkylation reaction zone, 22.40 lb-moles/hr. (10.18 kg-moles/hr.), is varied as hereafter described. The 61.40 lb-moles/hr. (27.91 kg-moles/hr.) which continue through line 21, containing control valve 56, to be recycled to the transalkylation reaction zone is maintained substantially constant.

As will be recognized by those possessing knowledge of product separation via fractional distillation, pressure control must commence by providing a pressure-sensing device in the overhead system, preferably proximate to the locus of vaporous overhead withdrawal.

In the accompanying drawing, two Pressure Recorder Controllers (PRC's) 34 and 35 are shown as monitoring the benzene column pressure proximate to the overhead removal by way of line 4. Also, the pressure is sensed downstream from the locus at which BF₃ stripper 12 vapors are admixed via line 5. PRC's 34 and 35 could be represented by a single PRC having both instrument lines 36 and 38 emanating therefrom; however, for the purpose of a clear understanding, two are shown, each with their individual instrument lines transmitting signals, line 36 to control valve 37 and line 38 to FRC 39. For the present control method, the two PRC's, 34 and 35 are not simultaneously functional, but indicate different embodiments of the invention. In either configuration, the signal developed by the selected PRC is ultimately used in the system to effect an adjustment in the flow rate of the vaporous material, in line 33, being recycled to the alkylation reaction zone. The change is sensed by Flow Recorder Controller (FRC) 46, by way of orifice meter 47 in line 33, and a signal is developed which represents the rate change. This signal is transmitted via instrument line 48 to FC 49, which monitors the flow rate of the vented stream in line 32. The adjustable setpoint of FC 49 is reset, and FC 49 transmits the appropriate signal to control valve 52 by way of instrument line 51. In a preferred embodiment, the flow rate of the vaporous phase recycled to the transalkylation reaction zone through line 21 is maintained substantially constant through the use of FRC 53 which senses the flow via orifice meter 54, and transmits the appropriate signal through instrument line 55 to control valve 56.

In one embodiment, PRC 34 senses the pressure in the overhead system of benzene column 2, develops and transmits a signal to control valve 37 which is appropriately adjusted to vary the flow of spill-back vapors in line 57 from the discharge of first compression stage 17. PRC 35 is not functional, and FRC 39 does not receive a signal via instrument line 38 to reset its adjustable set point. To illustrate this embodiment, it will be presumed that something has taken place which causes a decrease in the overhead pressure of benzene column 2. PRC 34 effects an opening of control valve 37, thereby increasing the quantity of vaporous spill-back through line 57. This, in turn, decreases the quantity of vapors continuing through line 18 into interstage drum 20; also, the pressure sensed in line 21 (proximate to interstage drum 20), by PRC 43, decreases. A signal is transmitted through instrument line 44 to control valve 45, and an opening thereof is effected such that the spill-back flow from second compression stage 22 increases to maintain pressure in interstage drum 20.

The virtually immediate effect is a decrease in the quantity of vaporous material available for recycle via lines 33 and 21 to the alkylation zone and transalkylation zone, respectively. It must be borne in mind that the flow to the latter zone is being maintained substantially constant; therefore, there exists a decrease in the flow rate through line 33. This is measured via orifice meter 47, and a corresponding signal is developed and generated by FRC 46. Instrument line 48 transmits this signal to FC 49 to effect a resetting of its adjustable setpoint; in turn, a signal is transmitted via instrument line 51 to control valve 52 which closes to produce a slight decrease in the vapors vented from the system via line 32. The net result of the foregoing is an increase in vapor flow within benzene column 2 which increases the pressure in the upper section of the column.

In the second embodiment, PRC 35 is being used to sense the pressure proximate to overhead vapor withdrawal in line 4, and PRC 34 is non-functional. Control valve 37 is completely closed, with the effect that line 57 may be said to be non-existent. This configuration is a particularly preferred technique for effecting the present control method. In this instance, the presumption will be that something occurs which causes increased vapor flow in benzene column 2 such that the overhead pressure increases. The increase is sensed by PRC 35 which transmits the proper signal, via instrument line 38 to FRC 39; the adjustable setpoint of the latter is accordingly reset and an appropriate signal transmitted, via instrument line 41 to control valve 42 which experiences a closing. Two effects result virtually immediately and simultaneously: (1) a lesser quantity of BF₃-containing stripping vapors are introduced into benzene column 2, by way of conduit 24; and, (2) the pressure on interstage drum 20 increases.

PRC 43 senses the increased pressure on interstage drum 20 and transmits a signal via instrument line 44 to control valve 45 which closes. A corresponding decrease in spill-back vapors through line 6 is experienced, with the result that the quantity of vapors available for recycle to the two reaction zones increases. Again, since the flow to the transalkylation reaction zone, via line 21, is maintained substantially constant, the flow through line 33 to the alkylation reaction zone increases. The increase is sensed by orifice meter 47 and FRC 46, the latter transmitting an appropriate signal to FC 49 via instrument line 48. The adjustable setpoint of FC 49 is reset, and control valve 52 effects an opening which results in an increase in the flow rate of vented material in line 32.

The foregoing is believed to illustrate clearly the pressure control technique of the present invention and the method by which it functions. As will be recognized by those possessing the requisite skill in the appropriate art, the method accomplishes the two principal objects which are unattainable in the prior art. First, the quantity of vaporous inert material vented from the system is controlled to approximate the quantity originally introduced into the system with the fresh olefinic feed stream. Secondly, large pressure surges which stem either from increased, or decreased vapor flow in the fractional distillation column, proceed through the system back to the reaction zone without creating detrimental pressure cycling within the column.

I claim as my invention:

1. In a process for alkylating an aromatic hydrocarbon with a normally gaseous olefinic feed stream containing a normally gaseous paraffinic contaminant, in an alkylation reaction zone and in contact with an alkylation catalyst comprising a boron halide-modified refractory inorganic oxide, to produce an alkylated aromatic hydrocarbon, in which process (1) alkylation reaction product effluent is separated, in a fractional distillation column, to provide a first liquid-phase of an alkylated aromatic concentrate, containing poly-alkylated aromatics, and a first vapor-phase of an unreacted aromatic concentrate, containing boron halide and said paraffinic contaminant; (2) said first vaporous phase is separated, in a separation zone, to provide a second liquid-phase, unreacted aromatic concentrate and a second vapor-phase rich in paraffinic contaminant and boron halide; and, (3) a first portion of said second vapor-phase is returned to said distillation column, a second portion is recycled to said alkylation reaction zone, a third portion is treated, in a treating zone, to remove boron halide and at least a portion of the resulting paraffinic contaminant-rich vapors are withdrawn from the process, the method of controlling the fractional distillation column pressure which comprises the steps of:
   a. sensing the pressure in said distillation column at a locus proximate to the withdrawal of said unreacted aromatic vapor-phase concentrate;
   b. developing a first signal representative of said distillation column pressure;
   c. adjusting the flow rate of the second portion of said second vapor phase being recycled to said alkylation reaction zone responsive to said first signal;
   d. developing a second signal representing the flow rate of the recycled portion of said second vapor phase; and,
   e. regulating the quantity of said paraffinic contaminant-rich vapors withdrawn from said process responsive to said second signal.

2. The pressure control method of claim 1 further characterized in that said first signal directly regulates the flow rate of the first portion of said second vapor-phase being returned to said fractional distillation column.

3. The pressure control method of claim 1 further characterized in that said first signal directly regulates the flow rate of a fourth portion of said second vapor-phase, being returned to said separation zone, and the flow rate of the first portion of said second vapor-phase, being returned to said fractional distillation column, is maintained substantially constant.

4. The pressure control method of claim 1 further characterized in that said olefinic feed stream comprises hydrocarbons having from about 2 to about 4 carbon atoms per molecule.

5. The pressure control method of claim 1 further characterized in that said aromatic hydrocarbon is benzene.

6. The pressure control method of claim 1 further characterized in that said boron halide is boron trifluoride.

7. The pressure control method of claim 4 further characterized in that said olefinic feed stream comprises ethylene.

8. In a process for alkylating an aromatic hydrocarbon with a normally gaseous olefinic feed stream containing a normally gaseous paraffinic contaminant, in an alkylation reaction zone and in contact with an alkylation catalyst comprising boron trifluoride-modified alumina, to produce a mono-alkylated aromatic hydrocarbon, in which process (1) alkylation reaction product effluent is separated, in a first fractional distillation column, to provide a first liquid-phase of an alkylated aromatic concentrate, containing poly-alkylated aromatic hydrocarbons, and a first vapor-phase of an unreacted aromatic concentrate, containing boron trifluoride and said paraffinic contaminants; (2) said first liquid-phase is separated, in a second fractional distillation column, to recover said alkylated aromatic concentrate and to provide a poly-alkylated aromatic concentrate; (3) said poly-alkylated aromatic concentrate is reacted, in a transalkylation reaction zone and in contact with a transalkylation catalyst comprising boron trifluoride-modified alumina to produce additional mono-alkylated aromatic hydrocarbons; (4) said first vaporous phase is separated, in a separation zone, to provide a second liquid-phase, unreacted aromatic concentrate and a second vapor-phase rich in paraffinic contaminants and boron trifluoride; (5) a first portion of said second vapor-phase is returned to said first fractional distillation column, a second portion is recycled to said alkylation reaction zone, a third portion is recycled to said transalkylation reaction zone, a fourth portion is treated, in a treating zone, to remove boron trifluoride, and at least a portion of the resulting paraffinic contaminant-rich vapors are withdrawn from the process, the method of controlling the first fractional distillation column pressure which comprises the steps of:
   a. sensing the pressure in said distillation column at a locus proximate to the withdrawal therefrom of said first vapor-phase of unreacted aromatic concentrate;
   b. developing a first signal representative of said distillation column pressure;
   c. maintaining the flow rate of the third portion of said second vapor-phase, being recycled to said transalkylation reaction zone, substantially constant;
   d. adjusting the flow rate of the second portion of said second vapor-phase, being recycled to said alkylation reaction zone, responsive to said first signal;
   e. sensing the flow rate of the second portion of said second vapor-phase and developing a second signal representative thereof; and,
   f. adjusting the quantity of said paraffinic concentrate-rich vapors, withdrawn from said process, responsive to said second signal.

9. The pressure control method of claim 8 further characterized in that said first signal directly adjusts the flow rate of the first portion of said second vapor-phase being returned to said fractional distillation column.

10. The pressure control method of claim 8 further characterized in that said first signal directly regulates the flow rate of a fifth portion of said second vapor-phase, being returned to said separation zone, and the flow rate of the first portion of said second vapor-phase, being returned to said fractional distillation column, is maintained substantially constant.

11. In a process for alkylating benzene with an ethylene feed stream containing ethane, in an alkylation reaction zone and in contact with an alkylation catalyst comprising boron trifluoride-modified alumina, to produce ethylbenzene, in which process (1) alkylation reaction product effluent is separated, in a first fractional distillation column, to provide a first liquid-phase of an ethylbenzene concentrate, containing polyethylbenzenes, and a first vapor-phase of an unreacted benzene concentrate, containing boron trifluoride and ethane; (2) said first liquid-phase is separated, in a second fractional distillation column, to recover said ethylbenzene and to provide a polyethylbenzene concentrate; (3) said polyethylbenzene concentrate is reacted, in a transalkylation reaction zone and in contact with a transalkylation catalyst comprising boron trifluoride-modified alumina, to produce additional ethylbenzene; (4) said first vaporous phase is separated, in a separation zone, to provide a second liquid-phase of benzene and a second vapor-phase rich in ethane and boron trifluoride; (5) a first portion of said second vapor-phase is returned to said first fractional distillation column, a second portion is recycled to said alkylation reaction zone, a third portion is recycled to said transalkylation reaction zone, a fourth portion is treated, in a treating zone, to remove boron trifluoride, and at least a portion of the resulting ethane-rich vapors are withdrawn from the process, the method of controlling the first fractional distillation column pressure which comprises the steps of:

a. sensing the pressure in said first distillation column at a locus proximate to the withdrawal therefrom of said first vapor-phase of the benzene concentrate;

b. developing a first signal representative of said first distillation column pressure;

c. maintaining the flow rate of the third portion of said second vapor-phase, being recycled to said transalkylation reaction zone, substantially constant;

d. adjusting the flow rate of the second portion of said second vapor-phase, being recycled to said alkylation reaction zone, responsive to said first signal;

e. sensing the flow rate of the second portion of said second vapor-phase and developing a second signal representative thereof; and, f. adjusting the quantity of said ethane-rich vapors, withdrawn from said process, responsive to said second signal.

* * * * *